United States Patent
Meijer et al.

(10) Patent No.: US 7,825,059 B2
(45) Date of Patent: Nov. 2, 2010

(54) PROCESS FOR PREPARING TRIOXEPANE COMPOSITION AND USE THEREOF IN CROSSLINKING POLYMERS

(75) Inventors: John Meijer, Deventer (NL); Leonardus Bernardus Gerhardus Maria Nijhof, Enter (NL); Herman Evert Roelofs, Epse (NL); Haimo Tonnaer, Deventer (NL); Roelof Van De Worp, Deventer (NL)

(73) Assignee: Akzo Nobel N.V., Arnhem (NL)

( * ) Notice: Subject to any disclaimer, the term of this patent is extended or adjusted under 35 U.S.C. 154(b) by 61 days.

(21) Appl. No.: 11/794,281

(22) PCT Filed: Sep. 27, 2005

(86) PCT No.: PCT/EP2005/054821

§ 371 (c)(1),
(2), (4) Date: Sep. 7, 2007

(87) PCT Pub. No.: WO2006/066984

PCT Pub. Date: Jun. 29, 2006

(65) Prior Publication Data

US 2008/0132651 A1 Jun. 5, 2008

Related U.S. Application Data

(60) Provisional application No. 60/648,988, filed on Jan. 31, 2005.

(30) Foreign Application Priority Data

Dec. 23, 2004 (EP) .................................. 04078494

(51) Int. Cl.
C07D 323/00 (2006.01)
C08J 3/24 (2006.01)
C08K 5/159 (2006.01)
(52) U.S. Cl. .................. 502/172; 525/50; 525/256; 525/387; 549/266
(58) Field of Classification Search .................. 502/172; 525/50, 256, 387; 549/266
See application file for complete search history.

(56) References Cited

FOREIGN PATENT DOCUMENTS

WO   WO 98/50354      11/1998
WO   WO 9850354 A1 *  11/1998

OTHER PUBLICATIONS

Adam et al. ["1,2,4-Trioxepanes: Synthesis and Mass Spectral Behaviour,'" Journal of the Chemical Society, Chemical Communications, (13), 798-9, (1972)].*
Kirk-Othmer [The Encyclopedia of Chemical Technology, 3rd Edition, vol. 17, p. 57, (1982)].*
Waldemar, Adam, et al., "1,2,4-Trioxepanes: Synthesis and Mass Spectral Behaviour," Journal of the Chemical Society, Chemical Communications, (13), 798-9, (1972).
Kirk-Othmer, The Encyclopedia of Chemical Technology, 3rd Edition, vol. 17, p. 57, (1982).

* cited by examiner

Primary Examiner—Kelechi C Egwim
(74) Attorney, Agent, or Firm—Kenyon & Kenyon LLP

(57) ABSTRACT

Process to prepare a trioxepane compound of the following formula (I) comprising less than 3.5 wt % of dialkyl peroxide based on the total amount of peroxides, said process comprising the steps of reacting a glycol compound of the formula $R^3CHOH—CH_2—C(CH_3)_2OH$ with hydrogen peroxide in the presence of an acid to form a glycol hydroperoxide, purifying the glycol hydroperoxide, reacting the purified glycol hydroperoxide with a ketone or aldehyde of the formula $R^1R^2CO$ in the presence of an acid to form the trioxepane compound, and purifying the trioxepane compound, wherein $R^1$, $R^2$, and $R^3$ are independently selected from hydrogen and a substituted or unsubstituted hydrocarbyl group, with the proviso that if $R^1$ and $R^2$ are both methyl groups, $R^3$ is not hydrogen. Initiator compositions comprising the so-prepared trioxepane compound are characterized by a high safe processing temperature in combination with a good crosslink efficiency.

18 Claims, No Drawings

PROCESS FOR PREPARING TRIOXEPANE COMPOSITION AND USE THEREOF IN CROSSLINKING POLYMERS

REFERENCE TO RELATED APPLICATION(s)

This application claims the benefit of U.S. Provisional Application No. 60/648,988 filed on Jan. 31, 2005.

The present invention relates to a process to prepare a specific trioxepane compound, an initiator composition comprising such a trioxepane compound, polymer modification processes using the trioxepane compound, and products resulting from these processes.

In the process of crosslinking polymers, e.g. thermoplastic polymers such as high-density polyethylene, it is common practice to use an initiator composition, e.g. a peroxide-based initiator composition. In these processes the polymer is given the shape of the (final) shaped article and the crosslink process is performed.

Trioxepane compounds are known in the art and are for example disclosed in Kirk-Othmer, *The Encyclopedia of Chemical Technology*, 3$^{rd}$ Edition Volume 17, 1982, p. 57. According to this disclosure, they can be prepared by reaction of a hydroxyl hydroperoxide with an aldehyde or ketone, specifically acetone, in the presence of an acid catalyst.

WO 98/50354 discloses the preparation of 1,2,4-trioxepane compounds using 62.58% pure hexylene glycol hydroperoxide and any one of the four ketones cyclohexanone, ethyl acetoacetate, acetone, and 2,4-pentadione. The product resulting from this reaction as described in the examples is a composition of 1,2,4-trioxepane and more than 4 wt % of the dialkyl peroxide. The dialkyl peroxide is inevitably formed during the preparation process. The resulting trioxepane composition is subsequently used as an initiator composition for crosslinking a thermoplastic polymer. In WO 98/50354 it is described that the crosslinking reaction only takes place in the presence of both the initiator composition and a co-agent. More specifically, the co-agent is triallyl cyanurate.

However, like most of the other initiators that have been used up to now, the peroxide-based initiator composition of WO 98/50354 suffers from the problem that it starts to decompose at a temperature below the one at which the crosslinkable polymer melts or at a temperature at which the crosslinkable polymer's viscosity is insufficiently low to make easy processing possible. Because of such early decomposition of known initiator compositions, the crosslinking process cannot take place in a homogeneous composition, therefore the quality of the shaped article is not optimal. Further, the early decomposition of the initiator may result in premature crosslinking of the crosslinkable polymer during processing. If early decomposition is to be prevented, the processing of the crosslinkable polymer comprising the initiator composition cannot take place at a temperature at which the crosslinkable polymer is in a molten state or has a sufficiently low viscosity. In that case the forming of the shaped article is an energy-consuming and very inefficient process, one which often results in a shaped article with an imperfect surface, non-homogeneous mechanical and physical properties, and low durability.

It is generally understood that a homogeneous distribution of the initiator in the crosslinkable polymer results in a more efficient and simpler crosslinking process and in a higher standard, more durable, and better crosslinked polymer. Hence, tumble-mixing or other forms of pre-processing of the initiator and the solid crosslinkable polymer have been suggested to achieve a homogeneous distribution of initiator in the crosslinkable polymer up to now.

It will be understood that the process of crosslinking polymers and the distribution of initiator composition in the crosslinkable polymer are subject to improvement. One way to achieve an improved distribution of the initiator composition in the crosslinkable polymer and an improved process to crosslink the crosslinkable polymer would be by mixing the initiator and the crosslinkable polymer in a more readily processable state.

There have been a few initiators up to now that do not decompose at a temperature below the melting temperature of e.g. certain types of (ultra) high-molecular weight polyethylene. One example is ethyl-O-benzoyl laurohydroximate. However, this is an initiator compound prepared using a process wherein toxic compounds are used, such as HCl gas and hydroxylammonium chloride. Besides, ethyl-O-benzoyl laurohydroximate is usable as an initiator for the crosslinking of crosslinkable polymers only in the presence of a co-agent such as triallyl cyanurate. The use of triallyl cyanurates in the crosslinking process is disadvantageous, as it adds another compound to the crosslinking process and, besides, it is thought that triallyl cyanurates can lower the safe processing temperature.

There is therefore a need for an initiator composition and a process to crosslink a crosslinkable polymer that do not suffer from the above drawbacks. More specifically, there is a need for an initiator composition for crosslinking polymers that is stable at a temperature at which the crosslinkable polymers melt or have a low viscosity to make easy processing and homogeneous distribution of the initiator composition possible, which composition is environmentally friendly, does not require a co-agent, and can be prepared without having to use toxic materials. There is a need in the art for a process to crosslink polymers wherein the polymers and the initiator can be mixed in a molten or low viscous state, in which process the processing to a shaped article and the crosslinking can take place simultaneously, and which results in a durable and processable crosslinked polymer.

According to the invention, a process is provided to prepare a trioxepane compound of the following formula (I)

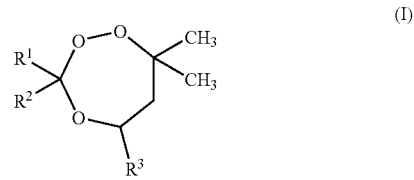

comprising less than 3.5 wt % of dialkyl peroxide based on the total amount of peroxides, said process comprising the steps of reacting a glycol compound of the formula R$^3$CHOH—CH$_2$—C(CH$_3$)$_2$OH with hydrogen peroxide in the presence of an acid to form a glycol hydroperoxide, purifying the glycol hydroperoxide, reacting the purified glycol hydroperoxide with a ketone or aldehyde of the formula R$^1$R$^2$CO in the presence of an acid to form the trioxepane compound, and purifying the trioxepane compound, wherein R$^1$, R$^2$, and R$^3$ are independently selected from hydrogen and a substituted or unsubstituted hydrocarbyl group, with the proviso that if R$^1$ and R$^2$ are both methyl groups, R$^3$ is not hydrogen.

According to the invention, an initiator composition is provided comprising a trioxepane compound of the following formula (I)

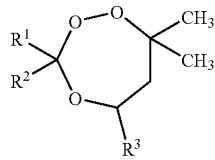

and 0 ppm to 3.5 wt % of a dialkyl peroxide compound of the formula (II)

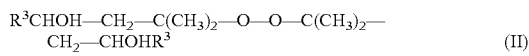

based on the total amount of peroxides, wherein $R^1$, $R^2$, and $R^3$ are independently selected from hydrogen and a substituted or unsubstituted hydrocarbyl group, and optionally two of the group of $R^1$, $R^2$, and $R^3$ are linked to form a ring structure, with the proviso that if $R^1$ and $R^2$ are both methyl groups, $R^3$ is not hydrogen.

The current invention further provides a process to prepare a crosslinked polymer wherein a reaction mixture comprising the crosslinkable polymer is brought to a temperature between 160° C. and 500° C., which is suitable for starting the crosslink reaction of the crosslinkable polymer in the presence of an initiator composition comprising a 1,2,4-trioxepane of the above formula (I) and 0 to 3.5 wt % on the total amount of peroxides of a dialkyl peroxide of formula (II). Also a masterbatch comprising a crosslinkable polymer and the initiator composition is provided.

The current invention moreover provides a crosslinked polymer obtainable by the process, a shaped article comprising such a crosslinked polymer, and a process to form a shaped article comprising a step wherein a crosslinkable polymer is processed to a desired shape and another step wherein the crosslinkable polymer is crosslinked. In the above process the crosslinking step preferably takes place simultaneously with or subsequent to the step of shaping the article. For thermoplastic (TPE) polymers, however, the crosslinking step preferably takes place before or simultaneously with the step of shaping the article.

When a 1,2,4-trioxepane compound is prepared by the conventional process, this conventional process comprising first reacting a glycol with hydroperoxide, subsequently reacting the glycol hydroperoxide with a ketone or aldehyde, where the second step is as disclosed in both the abovementioned Kirk-Othmer's *Encyclopedia of Chemical Technology* and WO98/50354, and subsequently purified by conventional methods like washing steps to remove undesired hydrogen peroxide and water-soluble byproducts to acquire a technically pure product, the amount of remaining dialkyl peroxide is found to be always at least about 4 wt %.

It has now been found that a trioxepane compound containing less than 3.5 wt % dialkyl peroxide can be prepared if the glycol hydroperoxide is purified between the two reaction steps. Preferably, the glycol hydroperoxide is purified such that it is more than 65% pure, more preferably more than 75% pure, even more preferably more than 85% pure, and most preferably more than 90% pure, based on the total amount of peroxides.

The initiator composition according to the present invention is characterised by an increased safe processing temperature, while at the same time a good crosslink efficiency is maintained. The increased safe processing temperature is related to a higher decomposition temperature of the initiator composition. An increased safe processing time means a decreased premature crosslinking of the crosslinkable polymer. As the crosslinkable polymer-containing initiator composition according to the invention has an increased safe processing temperature, it can be processed at temperatures higher than 160° C., preferably higher than 170° C., even more preferably higher than 175° C., without premature crosslinking resulting. Moreover, because the crosslinkable polymer can be crosslinked in a low viscous or molten state, the processing thereof to shaped objects is significantly easier and can take place simultaneously with the crosslinking of the crosslinkable polymer in the presence of the initiator composition, for example by extruding the molten polymer. An additional benefit of being able to add the initiator composition to molten crosslinkable polymer is that the resulting crosslinked polymer is more evenly crosslinked, which is demonstrated by an improved durability and a better surface of the crosslinked polymer. As an additional benefit a reduced occurrence of bubble formation has been found in the crosslinked polymer.

In the process to prepare a trioxepane compound in a purified state the purification of the glycol hydroperoxide and the 1,2,4-trioxepane compound may be by any conventional purification method. The purification of the glycol hydroperoxide preferably is done by extraction, crystallisation, filtration, solvent evaporation or a combination of one or more of these purification methods. The purification of the 1,2,4-trioxepane compound preferably is done by extraction, distillation, solvent evaporation or a combination of one or more of these purification methods. The purification step(s) may be repeated one or more times.

Preferred 1,2,4-trioxepane compounds of formula (I) and dialkyl peroxides of formula (II) are those wherein $R^{1-3}$ are independently selected from the group consisting of hydrogen and substituted or unsubstituted $C_1$-$C_{20}$ alkyl, $C_3$-$C_{20}$ cycloalkyl, $C_6$-$C_{20}$ aryl, $C_7$-$C_{20}$ aralkyl, and $C_7$-$C_{20}$ alkaryl, which groups may include linear or branched alkyl moieties, while two of the groups $R^{1-3}$ may be connected to form a (substituted) cycloalkyl ring; the optional one or more substituents on each of $R^1$-$R^3$ being selected from the group consisting of hydroxy, alkoxy, linear or branched alk(en)yl, aryloxy, halogen, carboxylic acid, ester, carboxy, nitrile, and amido. It should be noted, however, that if $R^1$ and $R^2$ are both methyl groups, $R^3$ is not hydrogen.

Preferably, $R^1$ and $R^3$ are selected from lower alkyl groups, more preferably $C_1$-$C_6$ alkyl groups, such as methyl, ethyl, and isopropyl, methyl and ethyl being most preferred. $R^2$ is preferably selected from hydrogen, methyl, ethyl, iso-propyl, iso-butyl, tert-butyl, amyl, iso-amyl, cyclohexyl, phenyl, $CH_3C(O)CH_2$—, $C_2H_5OC(O)CH_2$—, $HOC(CH_3)_2CH_2$—, and

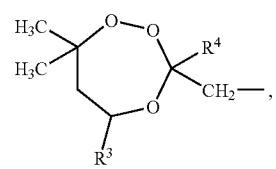

wherein R⁴ is independently selected from any of the group of compounds given for R¹⁻³. Another preferred product is:

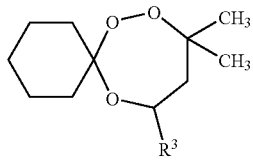

The initiator composition preferably comprises at least 1 ppm dialkyl peroxide, more preferably at least 10 ppm, and even more preferably at least 100 ppm dialkyl peroxide. In the most preferred embodiment the amount is at least 500 ppm. The initiator composition preferably comprises less than 3 wt % dialkyl peroxide, more preferably less than 2.5 wt %, and even more preferably less than 2 wt %. In the most preferred embodiment the amount of dialkyl peroxide is less than 1 wt %. All amounts of dialkyl peroxide are based on the total amount of peroxides in the composition.

The amount of trioxepane compound in the initiator composition in general is above 85 wt %. Preferably, the amount is more than 91%, more preferably more than 92 wt %, and most preferably more than 95%. The amount of trioxepane compound generally is less than 100 wt %, preferably less than 99.9 wt %. All amounts of trioxepane compound are based on the total amount of peroxides in the composition.

Crosslinkable polymers are crosslinkable polymers that can be cured with peroxide initiators. The crosslinkable polymers include but are not limited to thermoplastic resins such as polyethylene (co)polymers, rubbers such as natural rubber, silicon rubber, fluor rubber, ethylene-propylene(diene) rubber, polybutadiene rubber, polyisoprene rubber, polychloropentane rubber, styrene butadiene rubber, polyurethane rubber, polysulfide rubber, and ethylene vinylacetate rubber, blends of rubbers, blends of rubbers and thermoplastics (TPEs), and blends of thermoplastics. Preferably, the crosslinkable polymer is a high-density polyethylene polymer (HDPE), a low-density polyethylene polymer (LDPE), a fluor rubber, a silicone rubber, a polybutadiene rubber, or an ethylene-propylene (diene) rubber (EP(D)M). Most preferably, the crosslinkable polymer is a high-density polyethylene.

The process to crosslink crosslinkable polymer in the presence of the initiator composition normally takes place at a temperature equal to or higher than the temperature suitable for starting the crosslinking. Preferably, the temperature is higher than 175° C., more preferably higher than 185° C., and most preferably higher than 190° C. Preferably, the temperature is below 400° C., more preferably below 350° C., and most preferably below 300° C.

The amount of initiator composition preferably is 0.1 to 20 mmol per 100 g of crosslinkable polymer, more preferably 0.5 to 15 mmol per 100 g, most preferably 1.0 to 10 mmol per 100 g of crosslinkable polymer.

The processing of the crosslinkable polymer can be done by any known method such as extrusion, injection moulding, roto-moulding, compression moulding, transfer moulding.

Particularly suitable shaped articles according to the invention are pipes, tubes, cables, profiles, belting, containers, etc. A preferred shaped article according to the present invention is a pipe or cable comprising a crosslinked polyethylene as crosslinked polymer.

The initiator composition according to the present invention can also be suitably used to modify the molecular weight (distribution) of thermoplastics and/or thermoplastic elastomers in order to change their rheological properties. Therefore, the present invention also relates to a process wherein the rheology of a polymer or copolymer is modified by means of free radicals, using the initiator composition according to the present invention. The initiator composition can be employed in processes such as the degradation of polypropylene, the grafting of monomers onto polymers (e.g. maleic anhydride on polypropylene), and the functionalisation of polyolefins. It can also be used for degradation processes near a flame front.

In these processes, the initiator composition can be contacted with the polymeric material by applying the initiator composition to the surface of a polymeric object, mixing it throughout a polymeric matrix (in the molten, dissolved, granulated, or powdered state), or incorporating it into the polymer during the polymerisation step. These processes can be performed according to conventional methods.

The amount of trioxepane compound to be used in these processes preferably is 0.001-15.0 wt %, more preferably 0.005-10.0 wt %, most preferably 0.01-5.0 wt %, based on the weight of polymeric material.

Polymers that can be degraded or functionalised using the initiator composition according to the invention include isotactic polypropylene, a-tactic polypropylene, syndiotactic polypropylene, alkylene/propylene copolymers such as ethylene/propylene random and block copolymers; propylene/diene monomer copolymers, propylene/styrene copolymers, poly(butene-1), poly(butene-2), polyisobutene, isoprene/isobutylene copolymers, chlorinated isoprene/isobutylene copolymers, poly(methylpentene), polyvinyl alcohol, polystyrene, poly(α-methyl)styrene, 2,6-dimethyl polyphenylene oxide, styrenics, and mixtures or blends of these polymers and/or with other non-degradable polymers. Typically, with the degradation some properties of the polymer are improved, such as tenacity of fibres, warpage of injection moulded articles, the transparency of polymer films, and/or flowability away from a flame front. The modification process of the present invention is particularly advantageous for various polypropylene processes such as fibre spinning, high speed injection moulding, and melt-blowing of non wovens.

Examples of suitable polymers which can be grafted by means of the initiator composition according to the present invention are copolymers and block copolymers of conjugated 1,3-dienes, and one or more copolymerisable monoethylenically unsaturated monomers such as aromatic monovinylidene hydrocarbons, halogenated aromatic monovinylidene hydrocarbons, (meth)acrylonitrile, alkyl (meth)acrylates, acrylamides, unsaturated ketones, vinyl esters, vinylidenes, and vinyl halides; ethylene/propylene copolymers and ethylene/propylene copolymers with other (poly)unsaturated compounds such as hexadiene-1,4, dicyclopentadiene and 5-ethylidene norbornene; polyolefins such as polyethylene, polypropylene, and copolymers thereof; and polyols including polyols which are essentially free of ethylenic unsaturation. Such polyols include polyalkylene polyether polyols having from 2-6 carbon atoms per monomeric unit and an Mn of 400-2000, polyhydroxyl-containing polyesters, hydroxy-terminated polyesters, and aliphatic polyols.

Suitable monomers for grafting onto the above-mentioned polymers are olefinic or ethylenically unsaturated monomers such as: substituted or unsubstituted vinyl aromatic monomers including styrene and α-methylstyrene; ethylenically unsaturated carboxylic acids and derivatives thereof such as (meth)acrylic acids, (meth)acrylic esters and glycidyl methacrylate; ethylenically unsaturated nitriles and amides such as acrylonitrile, methacrylonitrile, and acrylamide; substituted or unsubstituted ethylenically unsaturated monomers such as butadiene; vinyl esters such as vinyl acetate and vinyl propionate; ethylenically unsaturated dicarboxylic acids and their derivatives including mono- and diesters, anhydrides, and imides, such as maleic anhydride, citraconic anhydride, citraconic acid, itaconic acid, nadic anhydride, maleic acid, aryl, alkyl, and aralkyl citraconimides and maleimides; vinyl halogenides such as vinyl chloride and vinylidene chloride; olefins such as isobutene and 4-methylpentene; and epoxides.

EXAMPLES

In the Examples the following methods are used.

Determination of the Safe Processing Temperature

The increase in melt viscosity of the crosslinked polymer samples was measured at the temperatures indicated in the tables below using an Alpha Technology Rheometer MDR 2000E. To determine the safe processing temperature the ts2 (min) was measured, ts2 (min) being the time from start of measurement to minimum viscosity+0.22 Nm. A higher ts2 (min) is directly related to an increased safe processing temperature.

Determination of the Crosslink Efficiency

For all polymers the Δ torque (represented by delta S in the tables) of the samples was measured using the Alpha Technology Rheometer MDR2000E. The delta torque is directly related to the crosslink efficiency.

In addition, for high-density polyethylene crosslinked polymer the crosslinking efficiency was also determined by means of the gel fraction after cure. The gel fraction was determined by adding 0.3 gram of crosslinked HDPE from the Rheometer to xylene, boiling the resulting mixture for 16 hours at a temperature of 136-138° C. During the boiling process the non-crosslinked HDPE was extracted from the xylene. After the boiling process the HDPE samples were washed with acetone and dried in a hot air oven for 2 hours and the sample was weighed again. The gel fraction is calculated as follows $$\text{Gel fraction} = \frac{weight_{after\ extraction}}{weight_{before\ extraction}} \cdot 100\%$$

The loss of weight is related to the amount of non-crosslinked polymer, hence the lower the gel fraction, the lower the crosslink efficiency. Further, the t90 (min) was measured, being the time needed to achieve 90% of total crosslinks.

Preparation of an Initiator Composition According to the Present Invention

Hexylene glycol hydroperoxide was prepared by reaction of 118.1 g (1.0 mol) hexylene glycol and 145.7 gr (3 mol) hydrogen peroxide in the presence of sulfuric acid at a temperature of 30° C. for 1 hour. The reaction mixture was cooled down to 20° C. and neutralized with sodium hydroxide until pH=6.8. After separation the underlayer was drained. The remaining crude hexylene glycol hydroperoxide was converted to sodium salt by the addition of 160 g of a 25% NaOH solution. Subsequently, the sodium salt was extracted 3 times with ethyl ether in order to lower the dialkyl peroxide content (di(3-hydroxy-1,1-dimethylbutyl)peroxide). The remaining sodium salt of hexylene glycol hydroperoxide was acidified with $H_2SO_4$ 25% until pH 3. Hexylene glycol hydroperoxide was isolated from the solution with ethyl ether. After evaporation of the ethyl ether the resulting product was analysed and found to contain 92% hexylene glycol hydroperoxide.

73 g (0.5 mol) of the above-prepared hexylene glycol hydroperoxide were reacted with 35 g (0.6 mol) of acetone in the presence of sulfuric acid at a temperature of 20° C. for 1 hour. After separation, the acid layer was removed and the crude trioxepane was washed once with a 4% NaOH solution. The trioxepane was dried on magnesium sulfate. The filtrated product was analysed and found to contain 95% 3,3,5,7,7-pentamethyl-1,2,4-trioxepane and 0.3% of dialkylperoxide (di(3-hydroxy-1,1-dimethylbutyl)peroxide).

(Comparative) Preparation Examples A to M

Using the above procedure, the following initiator compositions were prepared.

| Initiator compositions | Trioxepane | amount of dialkyl-peroxide (wt % on total peroxides) | Dialkylperoxide |
|---|---|---|---|
| A | 3,3,5,7,7-pentamethyl-1,2,4-trioxepane | 0.20 | di(3-hydroxy-1,1-dimethylbutyl)peroxide |
| B | 3,3,5,7,7-pentamethyl-1,2,4-trioxepane | 0.28 | di(3-hydroxy-1,1-dimethylbutyl)peroxide |
| C | 3,3,5,7,7-pentamethyl-1,2,4-trioxepane | 0.80 | di(3-hydroxy-1,1-dimethylbutyl)peroxide |
| D | 3,3,5,7,7-pentamethyl-1,2,4-trioxepane | 2.20 | di(3-hydroxy-1,1-dimethylbutyl)peroxide |
| E | 3,3,5,7,7-pentamethyl-1,2,4-trioxepane | 3.10 | di(3-hydroxy-1,1-dimethylbutyl)peroxide |
| F (Comparative) | 3,3,5,7,7-pentamethyl-1,2,4-trioxepane | 4.00 | di(3-hydroxy-1,1-dimethylbutyl)peroxide |
| G (Comparative) | 3,3,5,7,7-pentamethyl-1,2,4-trioxepane | 4.50 | di(3-hydroxy-1,1-dimethylbutyl)peroxide |
| H | 3-ethyl-3,5,7,7-tetramethyl-1,2,4-trioxepane | 0.10 | di(3-hydroxy-1,1-dimethylbutyl)peroxide |
| I | 3-ethyl-3,5,7,7-tetramethyl-1,2,4-trioxepane | 1.95 | di(3-hydroxy-1,1-dimethylbutyl)peroxide |
| J | 3-ethyl-3,5,7,7-tetramethyl-1,2,4-trioxepane | 2.88 | di(3-hydroxy-1,1-dimethylbutyl)peroxide |
| K (Comparative) | 3-ethyl-3,5,7,7-tetramethyl-1,2,4-trioxepane | 3.80 | di(3-hydroxy-1,1-dimethylbutyl)peroxide |
| L (Comparative) | — | 100 | Di-tert-butylperoxide |
| M (Comparative) | — | 100 | 2,5-dimethyl-2,5-di(tert-butylperoxy)hexyne, 85% in mineral oil |

(Comparative) Examples 1 to 11

Determination of Safe Processing Time and Crosslink Efficiency of Initiator Compositions in Crosslinking of High-Density Polyethylene To 100 g HDPE (Lupolen 5216Z ex Elenac) in a 250 ml pot an initiator composition was added and the reaction mixture was tumble-mixed for 30 minutes at ambient temperature. The amount of initiator composition was such that 5 mmol trioxepane was present per 100 g of polyethylene. After 16 hours the sample was put on the Rheometer and the ts2 (min) was measured. After the sample had reached the maximum torque, it was removed from the Rheometer and the crosslink efficiency (gel fraction) of the product was determined.

The results are as follows:

|  | Example | | | | |
| --- | --- | --- | --- | --- | --- |
|  | 1 | 2 | 3 | 4 | 5 (comp.) |
| Initiator composition | A | C | D | E | F |
| ts2 (min) at 180° C. | 22.6 | 9.50 | 2.90 | 1.97 | 1.76 |
| ts2 (min) at 200° C. | 3.66 | 1.84 | 0.97 | 0.81 | 0.76 |
| t90 (min) at 200° C. | 36.6 | 16.5 | 14.8 | 13.9 | 13.8 |
| Delta S (Nm) at 200° C. | 1.25 | 1.34 | 1.34 | 1.33 | 1.32 |
| Gel fraction (%) | 88.9 | 89.8 | 88.3 | 85.6 | 88.8 |

|  | Example | | | | | |
| --- | --- | --- | --- | --- | --- | --- |
|  | 6 | 7 | 8 | 9 (comp.) | 10 (comp.) | 11 (comp.) |
| Initiator composition | H | I | J | K | L | M |
| ts2 (min) at 180° C. | 2.74 | 1.61 | 1.30 | 1.23 | 0.84 | 0.78 |
| t90 (min) at 180° C. | 25.0 | 24.5 | 23.9 | 24.2 | 7.07 | 11.5 |
| Delta S (Nm) at 180° C. | 1.44 | 1.37 | 1.37 | 1.37 | 1.79 | 2.14 |
| ts2 (min) at 200° C. | 0.82 | 0.69 | 0.70 | 0.63 | 0.45 | 0.46 |
| t90 (min) at 200° C. | 5.77 | 5.76 | 5.63 | 5.94 | 1.60 | 2.40 |
| Delta S (Nm) at 200° C. | 1.44 | 1.36 | 1.36 | 1.33 | 1.80 | 2.04 |
| Gel fraction (%) | 95.5 | 94.3 | 95.8 | 94.9 | 99.0 | 98.8 |

(Comparative) Examples 12 and 13

Determination of Safe Processing Time and Crosslink Efficiency of Initiator Compositions in Crosslinking of Silicone Rubbers To 100 g crosslinkable silicone rubber (Silopren HV3/611U ex GE Bayer) an initiator composition was added and the whole was mixed on a Dr. Collin two-roll mill for 5 minutes at ambient temperature. The amount of initiator composition was chosen such that 2 mmol was present per 100 g of silicone rubber. After mixing the compound was put on the Rheometer and the ts2 and the crosslinking efficiency (Δ torque) were measured.

The results are given in the table below.

|  | Example | |
| --- | --- | --- |
|  | 12 | 13 (comp.) |
| Initiator composition | B | G |
| ts2 (min). at 200° C. | 1.85 | 1.10 |
| t90 (min). at 200° C. | 7.2 | 8.3 |
| Delta S (Nm) at 200° C. | 0.61 | 0.63 |

As demonstrated, the safe processing temperature (ts$_2$) in silicon rubber of the initiator composition according to the invention having a low dialkyl content is significantly higher than that of the comparative initiator composition having a high dialkyl content.

(Comparative) Examples 14 and 15

Determination of Safe Processing Time and Crosslink Efficiency of Initiator Compositions in Crosslinking of EPDM-Rubbers To a crosslinkable EPDM rubber compound (100 g EPDM, Keltan 578 (ex DSM), 70 g carbon black SRF, 70 g carbon black FEF (ex Cabot), and 50 g oil (Sunpar 2280; ex Sunoco oil) an initiator composition was added and the whole was mixed on a Dr. Collin two-roll mill for 5 minutes at 60° C. The amount of initiator composition was chosen such that 14 mmol trioxepane per 100 g rubber was used. After mixing, the compound was put on the Rheometer and the ts2 and the crosslinking efficiency (Δ torque) were measured.

The results are given in the table below.

|  | Example | |
| --- | --- | --- |
|  | 14 | 15 (comp.) |
| Initiator composition | B | G |
| ts2 (min) at 200° C. | 10.6 | 8.5 |
| t90 (min) at 200° C. | 22.9 | 22.0 |
| Delta S (Nm) at 200° C. | 0.35 | 0.39 |
| ts2 (min) at 220° C. | 2.7 | 2.2 |
| t90 (min) at 220° C. | 6.3 | 5.7 |
| Delta S (Nm) at 220° C. | 0.36 | 0.37 |

As demonstrated, the safe processing temperature (ts$_2$) in EPDM rubber of the initiator composition having a low dialkyl content is significantly higher than that of the initiator composition having a high dialkyl content.

Examples 16 to 23

Safe Processing Time Depending on the Amount of Initiator Composition Used in the Crosslinking of HDPE To 100 g HDPE (Lupolen 5216Z ex Elenac) in a 250 ml pot an initiator composition was added and the reaction mixture was tumble-mixed for 30 minutes at ambient temperature. The amount of initiator composition was such that 2, 5, 10, 17.2 or 17.3 mmol trioxepane was present per 100 g of polyethylene. After 16 hours the sample was put on the Rheometer and the ts2/min was measured. After the sample had reached the maximum torque, it was removed from the Rheometer and the crosslink efficiency (gel fraction) of the product was determined.

The results are given in the tables below.

|  | Example | | | |
| --- | --- | --- | --- | --- |
|  | 16 | 17 | 18 | 19 |
| Initiator composition | C | C | C | C |
| Amount in mmol trioxepane/100 g HDPE | 2 | 5 | 10 | 17.2 |
| ts2 (min) at 180° C. | 24.6 | 9.50 | 4.90 | 2.49 |
| ts2 (min) at 200° C. | 3.68 | 1.84 | 1.06 | 0.82 |
| t90 (min) at 200° C. | — | 16.50 | 11.58 | 9.93 |
| t90 (min) at 220° C. | 7.23 | 3.94 | | |
| Delta S (Nm) at 200° C. | 1.27 | 1.34 | 1.38 | 1.33 |
| Gel fraction (%) | 90.9 | 89.8 | 89.8 | 95.8 |

|  | Example | | | |
| --- | --- | --- | --- | --- |
|  | 20 | 21 | 22 | 23 |
| Initiator composition | H | H | H | H |
| Amount in mmol trioxepane/100 g HDPE | 2 | 5 | 10 | 17.3 |
| ts2 (min) at 180° C. | 5.75 | 2.78 | 1.70 | 1.15 |
| ts2 (min) at 200° C. | 1.48 | 0.84 | 0.67 | 0.52 |
| t90 (min) at 200° C. | 13.2 | 6.31 | 4.44 | 2.68 |
| Delta S (Nm) at 200° C. | 1.28 | 1.45 | 1.47 | 1.71 |
| Gel fraction (%) | 88.1 | 93.5 | 94.7 | 97.8 |

From the above table it can be seen that the safe processing temperature, as expressed in ts2, and the crosslinking time, as expressed in t90, decrease when the amount of initiator increases.

(Comparative) Examples 24-26

Polypropylene Degradation

Initiator composition A (when used) was dissolved in dichloromethane (approx. 5 wt % solution) and mixed with polypropylene (PP) powder in an amount of 0 (Comparative Example 24), 0.325 (Example 25) or 0.65 (Example 26) meq peroxide/100 g PP. The mixtures were placed in a fume cupboard for 4 hours to remove dichloromethane. In addition, 0.05% by weight of Irganox 1010 (antioxidant) powder, based on the weight of PP, was mixed in.

The resulting mixture was fed into a Haake Rheocord system 40 with Rheomex TW100 intensive mixing screws using a Plasticolor 2000 single screw feeder with screw housing type 15/22. In order to maintain low-oxygen conditions, nitrogen was introduced into the hopper (2.5 ltr/min) and around the die (9 ltr/min). During extrusion the screw speed was set to 50 rpm and the temperature settings were 190/250/250/250° C. The resulting strand was cooled using a water bath and granulated using an Automatik ASG5 granulator.

Before analysis the granules were dried overnight in a circulation oven at 60° C. The melt flow index (MFI) of the polymer was analysed in the conventional way using method ASTM D1238 (230° C./2.16 kg).

The results are given in the Table below. It shows that the initiator composition according to the present invention can be suitably used for polypropylene degradation.

|  | Example | | |
| --- | --- | --- | --- |
|  | 24 (comp) | 25 | 26 |
| Initiator composition A (% on PP) | — | 0.06% | 0.12% |
| meq peroxide/100 gram PP | — | 0.325 | 0.65 |
| MFI (g/10 min) | 3 | 318 | >400 |
| (230° C./2.16 kg density 0.72 g/ml) | | | |

(Comparative) Examples 27-29

Maleic Anhydride Grafting onto Polypropylene

Initiator composition A (when used) was dissolved in dichloromethane (approx. 5% weight solution) and mixed with a propylene homopolymer (grade HC001A-B1 ex Borealis) in an amount of 0 (Comparative Example 27), 0.5 (Example 28) or 1.0 (Example 29) meq peroxide/100 g PP.

The mixtures were placed in a fume cupboard for 4 hours to remove the dichloro-methane. Subsequently, 0.05% by weight of Irganox 1010 (antioxidant) and 1% by weight of maleic anhydride (MAH) powder, both based on the weight of PP, were mixed in.

The resulting mixture was fed into a Haake Rheocord system 9000 with Rheomex TW100 intensive mixing screws using a Plasticolor 2000 single screw feeder with screw housing type 15/22. In order to maintain low-oxygen conditions, nitrogen was introduced into the hopper (2.5 ltr/min) and around the die (9 ltr/min). During extrusion the screw speed was set to 80 rpm and the temperature settings were 160/220/220/220° C. The resulting strand was cooled using a water bath and granulated using an Automatik ASG5 granulator.

Before analysis the granules were dried overnight in a circulation oven at 60° C. The MFI of the polymer was analysed in the conventional way using method ASTM D1238 (190° C./2.16 kg).

To remove non-grafted MAH, the dried polymer was extracted with 80 ml of a mixture of dichloromethane/cyclohexane 3:1 V/V for 3 hours in the boiling mode and 1 hour in the rinsing mode in a Tecator Soxtec System HT2 (1045 Extraction unit+1046 Service unit). Subsequently, the extracted polymer was vacuum dried overnight in a vacuum oven at 70° C. The extracted and dried polymer was used to press film material in a Fontijne press.

The conditions used were:

1.3 grams of polymer 1 min at 190° C./10 kN 1 min at 190° C./50 kN 1 min at 190° C./150 kN 1 min at 30° C./150 kN The obtained film material was used to analyse the MAH grafting index by Infrared measurement using a Bruker Vector 22 FT-IR. This index is defined as the absorbance ratio of the MAH peak at 1790 cm-1 and the PP peak at 1167 cm-1 (correction for film thickness) multiplied by 100.

The results are shown in the table below. It shows that the initiator composition according to the present invention can be suitably used for maleic anhydride grafting onto polypropylene.

|  | Example | | |
| --- | --- | --- | --- |
|  | 27 (comp.) | 28 | 29 |
| Polypropylene | 100 | 100 | 100 |
| Irganox 1010 ex Ciba (phr*) | 0.05 | 0.05 | 0.05 |
| Maleic anhydride (MAH) powder (phr) | 1 | 1 | 1 |
| Initiator composition A (phr) | — | 0.085 | 0.170 |
| meq peroxide/100 gram PP | | 0.5 | 1.0 |
| Torque (Nm) | 46 | 36 | 36 |
| MFI (190° C./2.16 kg) g/10 min (density 0.77 g/ml) | 1.1 | 112 | 145 |
| MAH grafting FTIR: AU at 1790 cm−1 | 0 | 0.040 | 0.056 |

-continued

| | Example | | |
|---|---|---|---|
| | 27 (comp.) | 28 | 29 |
| PP (film thickness) FTIR: AU at 1167 cm−1 | 0.709 | 0.478 | 0.426 |
| MAH grafting index | 0 | 8.4 | 13.1 |

*per hundred resin

The invention claimed is:

1. A process to prepare a trioxepane compound of the following formula (I)

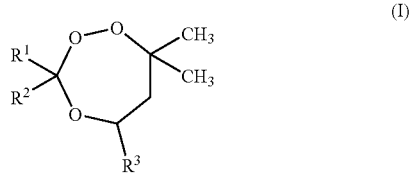
(I)

comprising at least 1 ppm to less than 3.5 wt % of dialkyl peroxide based on the total amount of peroxides, said process comprising the steps of reacting a glycol compound of the formula $R^3CHOH\text{---}CH_2\text{---}C(CH_3)_2OH$ with hydrogen peroxide in the presence of an acid to form a glycol hydroperoxide, purifying the glycol hydroperoxide, reacting the purified glycol hydroperoxide with a ketone or aldehyde of the formula $R^1R^2CO$ in the presence of an acid to form the trioxepane compound, and purifying the trioxepane compound, wherein $R^1$, $R^2$, and $R^3$ are independently selected from hydrogen and a substituted or unsubstituted hydrocarbyl group, with the proviso that if $R^1$ and $R^2$ are both methyl groups, $R^3$ is not hydrogen.

2. An initiator composition comprising a trioxepane compound of the formula (I)

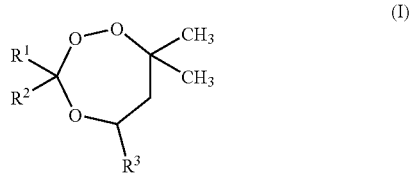
(I)

and 1 ppm to 3.5 wt % of a dialkyl peroxide compound of the formula (II)

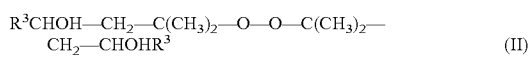
(II)

based on the total amount of peroxides, wherein $R^1$, $R^2$, and $R^3$ are independently selected from hydrogen and a substituted or unsubstituted hydrocarbyl group, and optionally two of the group of $R^1$, $R^2$, and $R^3$ are linked to form a ring structure, and wherein if $R^1$ and $R^2$ in the trioxepane compound of formula (I) are both methyl groups, $R^3$ is not hydrogen.

3. The initiator composition according to claim 2 wherein $R^1$ and $R^3$ are selected from lower alkyl groups, such as methyl, ethyl, and isopropyl, $R^2$ is selected from hydrogen, methyl, ethyl, iso-propyl, iso-butyl, tert-butyl, amyl, iso-amyl, cyclohexyl, phenyl, $CH_3C(O)CH_2\text{---}$, $C_2H_5OC(O)CH_2\text{---}$, $HOC(CH_3)_2CH_2\text{---}$, and

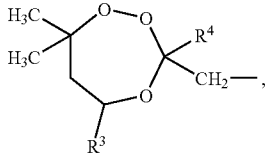

wherein $R^4$ is independently selected from any of the group of compounds given for $R^{1-3}$.

4. A process to crosslink a crosslinkable polymer wherein a reaction mixture comprising the crosslinkable polymer is brought to a temperature suitable for starting the crosslink reaction of the crosslinkable polymer in the presence of an initiator composition of claim 2.

5. The process according to claim 4, wherein in the initiator composition, $R^1$ and $R^3$ are selected from lower alkyl groups, such as methyl, ethyl, and isopropyl, $R^2$ is selected from hydrogen, methyl, ethyl, iso-propyl, iso-butyl, tert-butyl, amyl, iso-amyl, cyclohexyl, phenyl, $CH_3C(O)CH_2\text{---}$, $C_2H_5OC(O)CH_2\text{---}$, $HOC(CH_3)_2CH_2\text{---}$, and

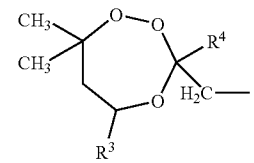

wherein $R^4$ is independently selected from any of the group of compounds given for $R^{1-3}$.

6. The process according to claim 4, wherein the temperature is 160 to 500° C.

7. The process according to claim 6, wherein the temperature is 170-400° C.

8. The process according to claim 4, further comprising a step wherein a crosslinkable polymer is processed to a desired shape, to form a shaped article.

9. The process according to claim 8, wherein the crosslinking step takes place simultaneously with or subsequent to the shaping step.

10. A process of modifying a polymer or copolymer comprising contacting the initiator composition of claim 2 with a polymeric material.

11. The process according to claim 10, wherein contacting the initiator composition with the polymeric material is in the presence of free radicals thereby modifying the rheology of the polymer or copolymer.

12. The process according to claim 11, wherein in the initiator composition is, $R^1$ and $R^3$ are selected from lower alkyl groups, such as methyl, ethyl, and isopropyl, $R^2$ is selected from hydrogen, methyl, ethyl, iso-propyl, iso-butyl, tert-butyl, amyl, iso-amyl, cyclohexyl, phenyl, $CH_3C(O)CH_2\text{---}$, $C_2H_5OC(O)CH_2\text{---}$, $HOC(CH_3)_2CH_2\text{---}$, and

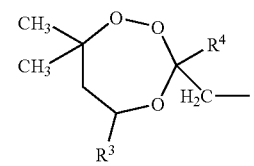

wherein $R^4$ is independently selected from any of the group of compounds given for $R^{1-3}$.

13. The process according to claim 11, wherein the polymer is polypropylene.

14. The process according to claim 10, wherein contacting the initiator composition with the polymeric material is in the presence of a monomer thereby grafting monomers onto the polymer.

15. The process according to claim 14, wherein in the initiator composition, $R^1$ and $R^3$ are selected from lower alkyl groups, such as methyl, ethyl, and isopropyl, $R^2$ is selected from hydrogen, methyl, ethyl, iso-propyl, iso-butyl, tert-butyl, amyl, iso-amyl, cyclohexyl, phenyl, $CH_3C(O)CH_2-$, $C_2H_5OC(O)CH_2-$, $HOC(CH_3)_2CH_2-$, and

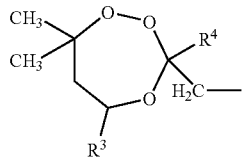

wherein $R^4$ is independently selected from any of the group of compounds given for $R^{1-3}$.

16. The process according to claim 14, wherein the polymer is polypropylene and the monomer is maleic anhydride.

17. A masterbatch comprising a crosslinkable polymer and an initiator composition of claim 2.

18. The masterbatch according to claim 17, wherein in the initiator composition, $R^1$ and $R^3$ are selected from lower alkyl groups, such as methyl, ethyl, and isopropyl, $R^2$ is selected from hydrogen, methyl, ethyl, iso-propyl, iso-butyl, tert-butyl, amyl, iso-amyl, cyclohexyl, phenyl, $CH_3C(O)CH_2-$, $C_2H_5OC(O)CH_2-$, $HOC(CH_3)_2CH_2-$, and

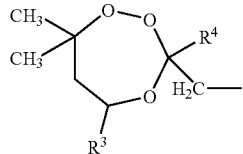

wherein $R^4$ is independently selected from any of the group of compounds given for $R^{1-3}$.

* * * * *